US00PP27658P3

(12) United States Plant Patent
Jordan et al.

(10) Patent No.: US PP27,658 P3
(45) Date of Patent: Feb. 14, 2017

(54) ***VACCINIUM* PLANT NAMED 'JAAC'**

(50) Latin Name: *Vaccinium corymbosum*
Varietal Denomination: JAAC

(71) Applicants: Lancelot Alan Jordan, Hamilton (NZ); Jeanette Jordan, Hamilton (NZ)

(72) Inventors: Lancelot Alan Jordan, Hamilton (NZ); Jeanette Jordan, Hamilton (NZ)

( * ) Notice: Subject to any disclaimer, the term of this patent is extended or adjusted under 35 U.S.C. 154(b) by 71 days.

(21) Appl. No.: 14/545,511

(22) Filed: May 14, 2015

(65) Prior Publication Data

US 2016/0338234 P1 Nov. 17, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Anne Grunberg

(57) ABSTRACT

A blueberry plant particularly distinguished by large oblate fruit with sweet flavour, crisp texture, strong blue colour and abundant bloom; rounded leaves with a puckered surface texture; upright plant habit with good vigour and green appearance and deciduous foliage, is described.

7 Drawing Sheets

Genus and species: *Vaccinium corymbosum.*
Variety denomination: 'JAAC'.

BACKGROUND OF THE INVENTION

The present invention relates to a new and distinct variety of *Vaccinium corymbosum* (blueberry) hereinafter referred to by the cultivar name 'JAAC' or the 'new plant'. 'JAAC' was discovered as a newly found seedling of unknown parentage in a commercial field plantation of 'Sunset Blue' (U.S. Plant Pat. No. 21,761) in February 2014 in Gordonton, Waikato, New Zealand.

The new plant has been asexually propagated by softwood cuttings in Cambridge, Waikato, New Zealand and the unique combination of characteristics of the new plant has been found to be reproducible and stable in propagation.

Plant Variety rights application for 'JAAC' was filed in New Zealand on 20 Mar. 2015 and assigned the application number BLU054. Propagation material of 'JAAC' has never been sold or made publically available prior to the filing of this application.

SUMMARY OF THE INVENTION

The following are the most outstanding and distinguishing characteristics of the new plant when grown under normal horticultural practices in Gordonton, Waikato, New Zealand:

1. Large oblate fruit with sweet flavour, crisp texture, strong blue colour and abundant bloom
2. Rounded leaves with a puckered surface texture
3. Upright plant habit with good vigour and green appearance
4. Deciduous foliage

DESCRIPTION OF THE PHOTOGRAPHS

The new plant is illustrated by the accompanying photographs which show in full color typical specimens of the plant habit, foliage, fruit and flowers of the new variety 'JAAC'.

Figure 1:
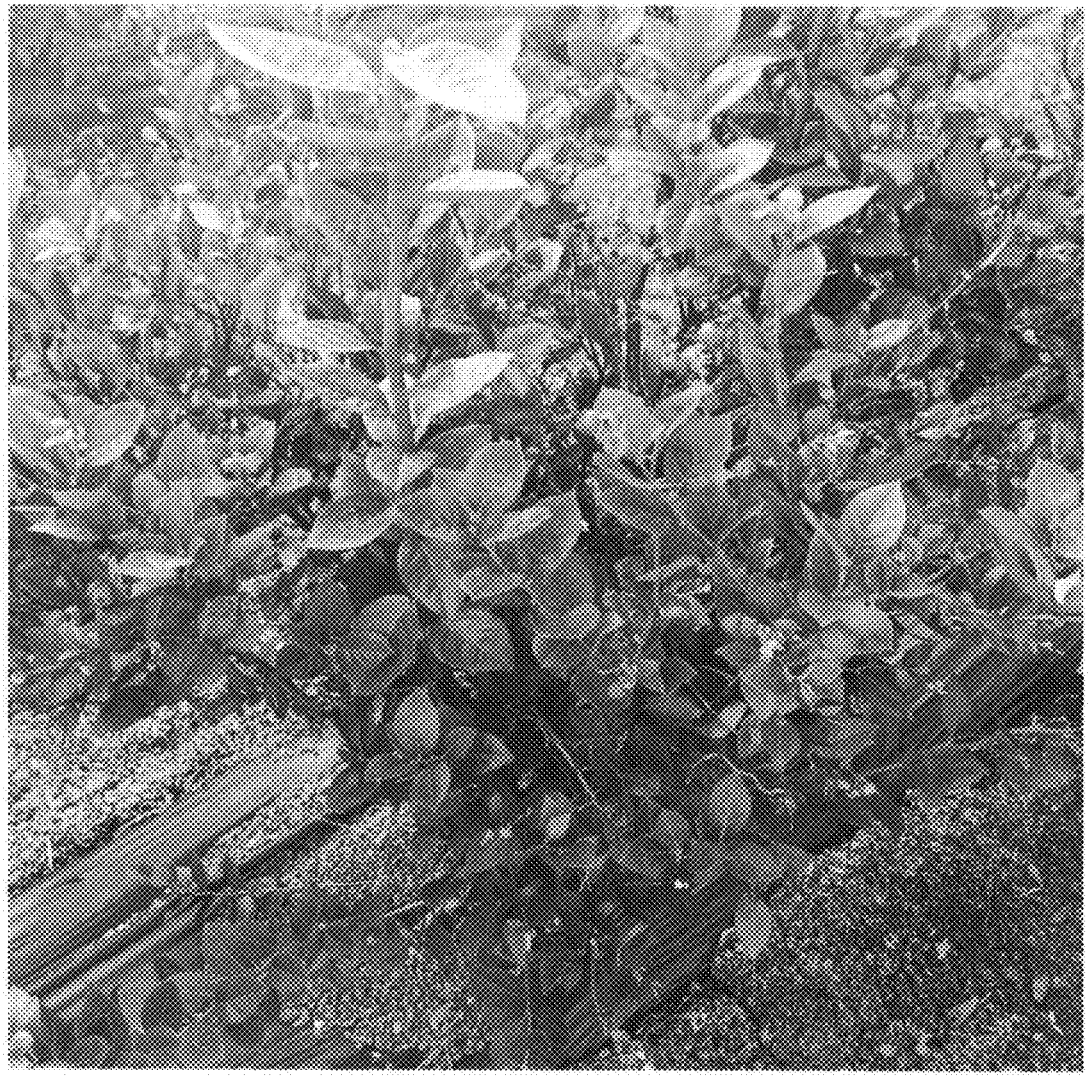
Figure 2:
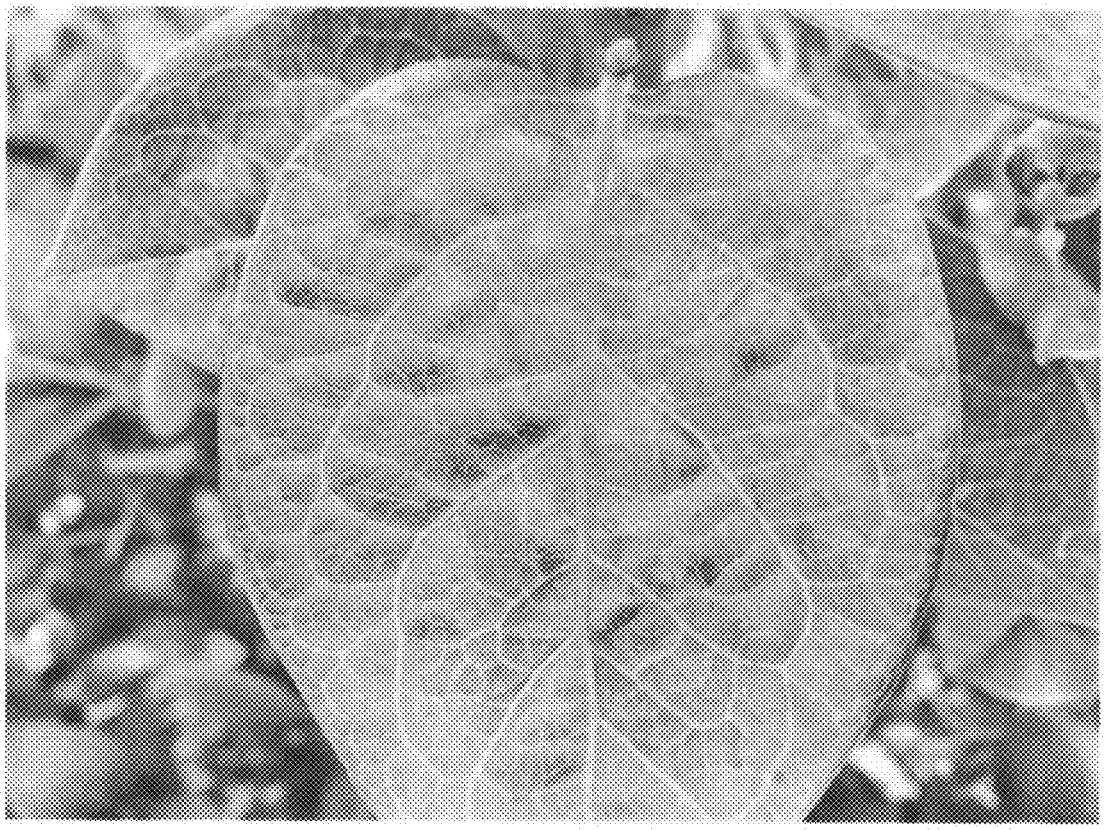
Figure 3:
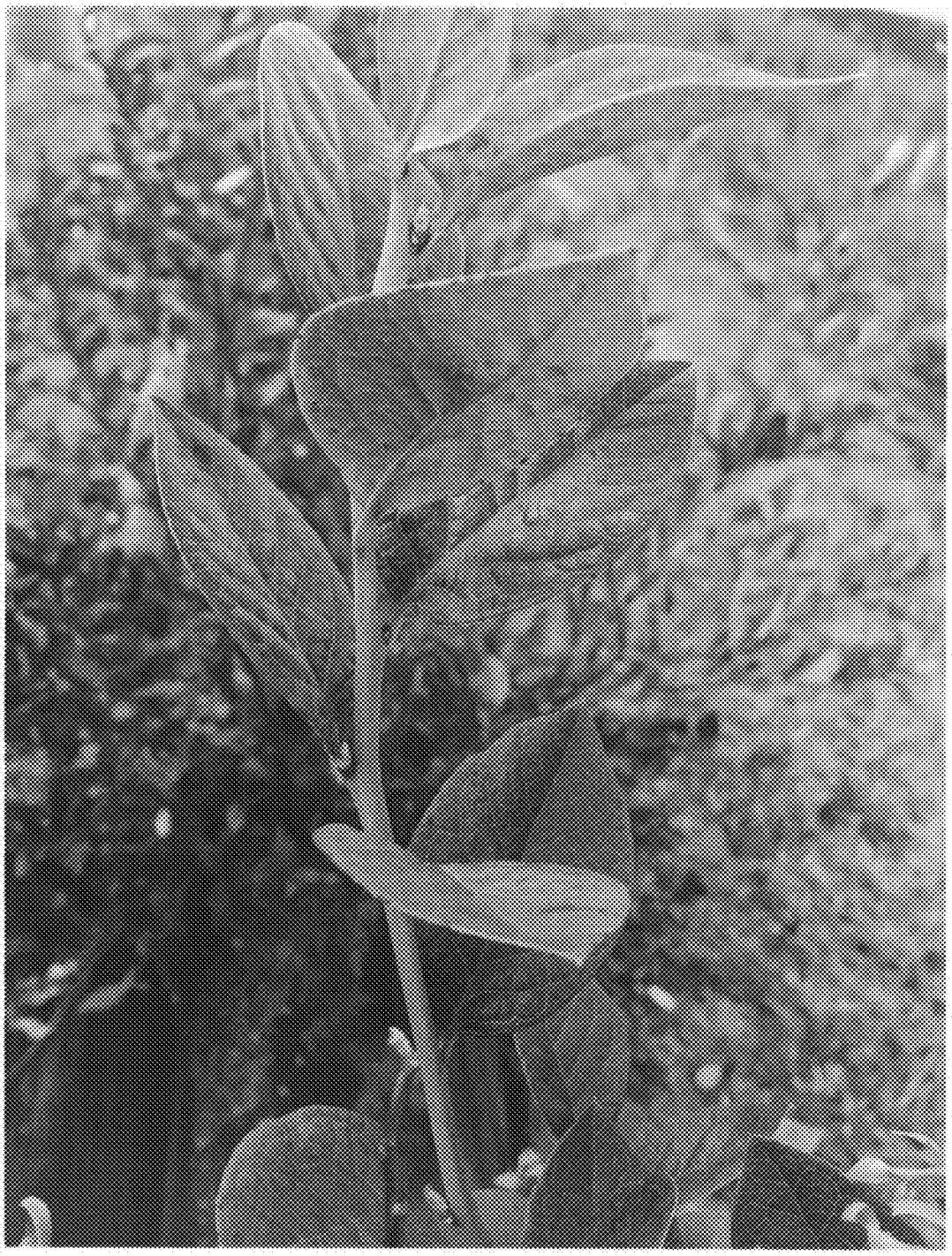
Figure 4:
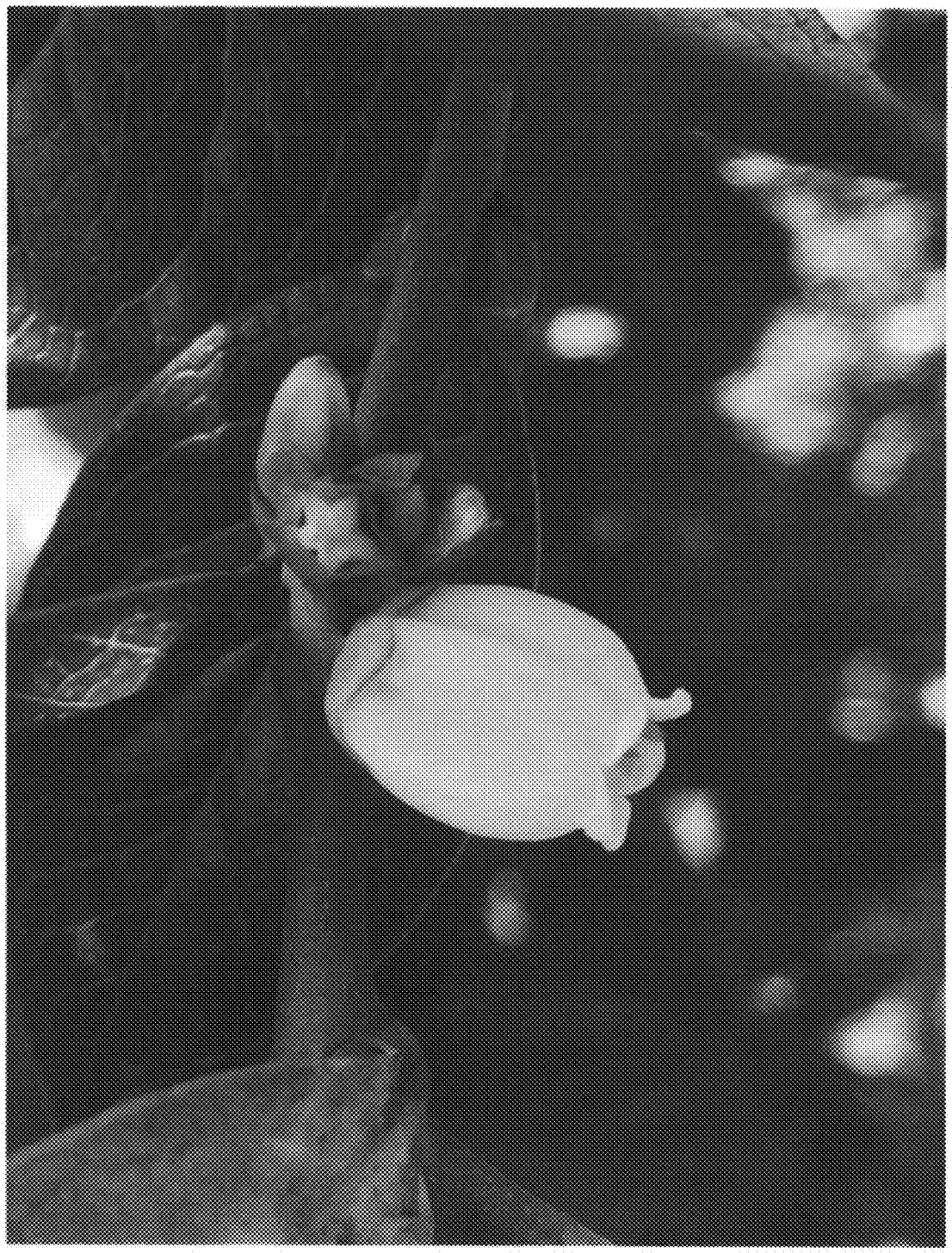
Figure 5:
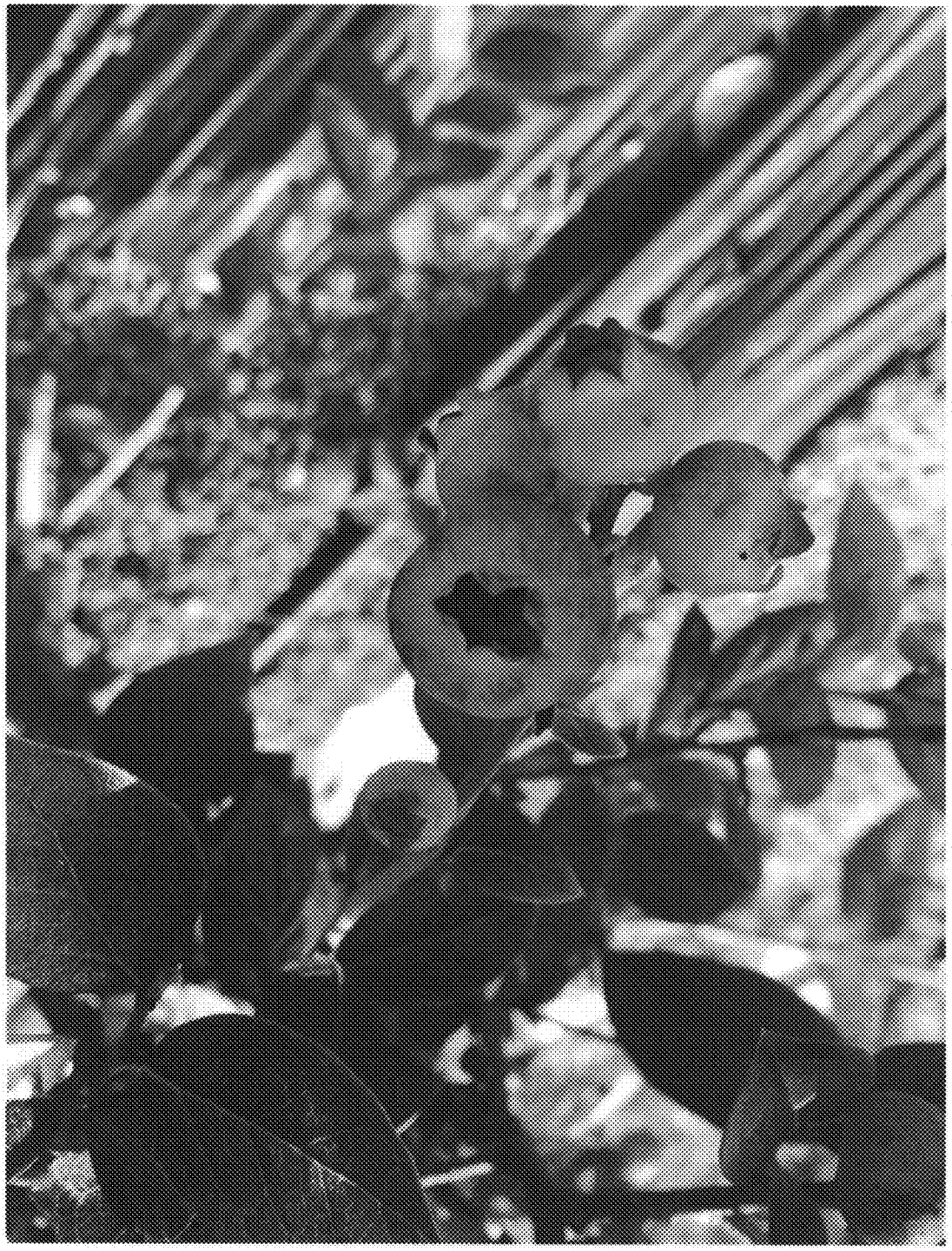
Figure 6:
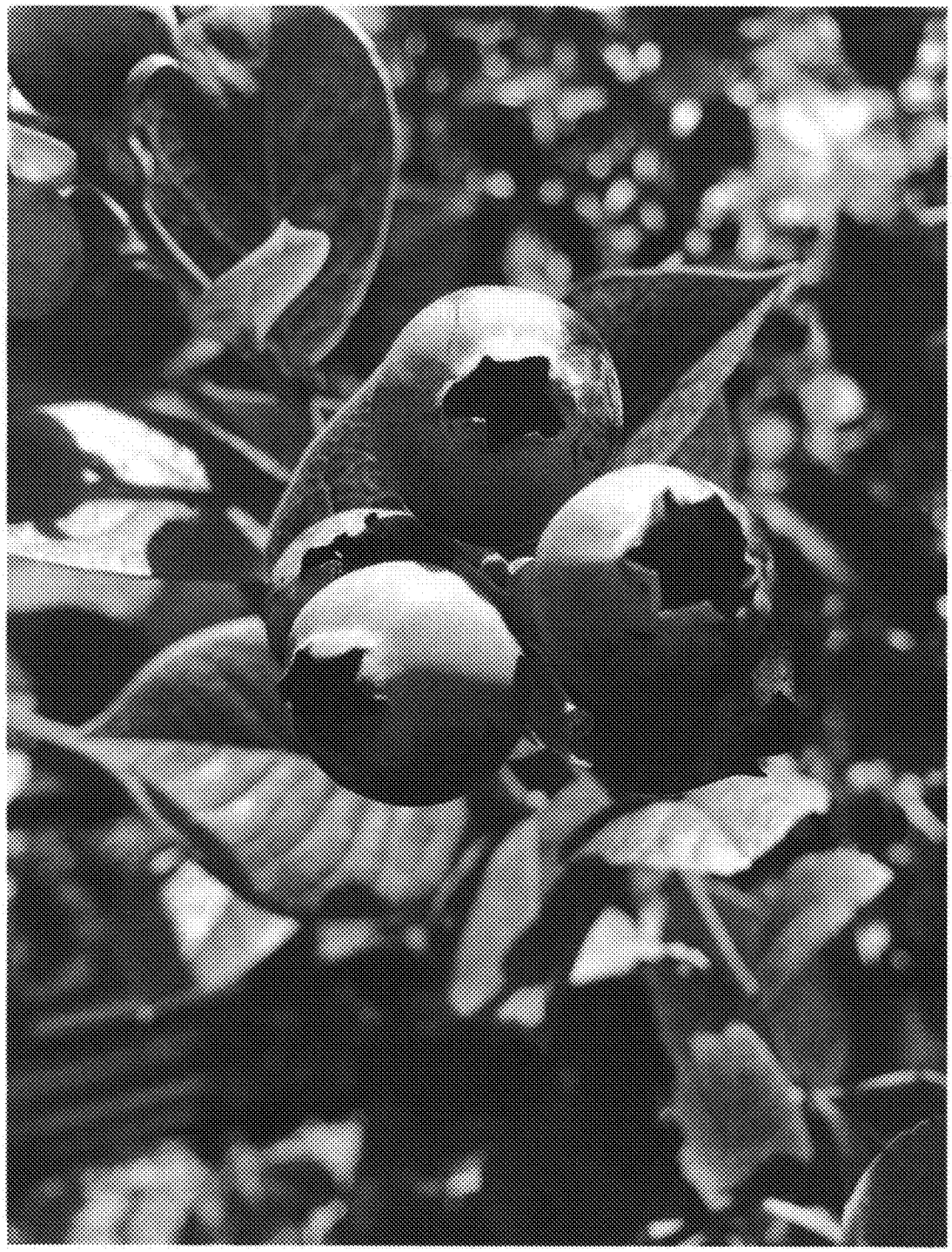
Figure 7:
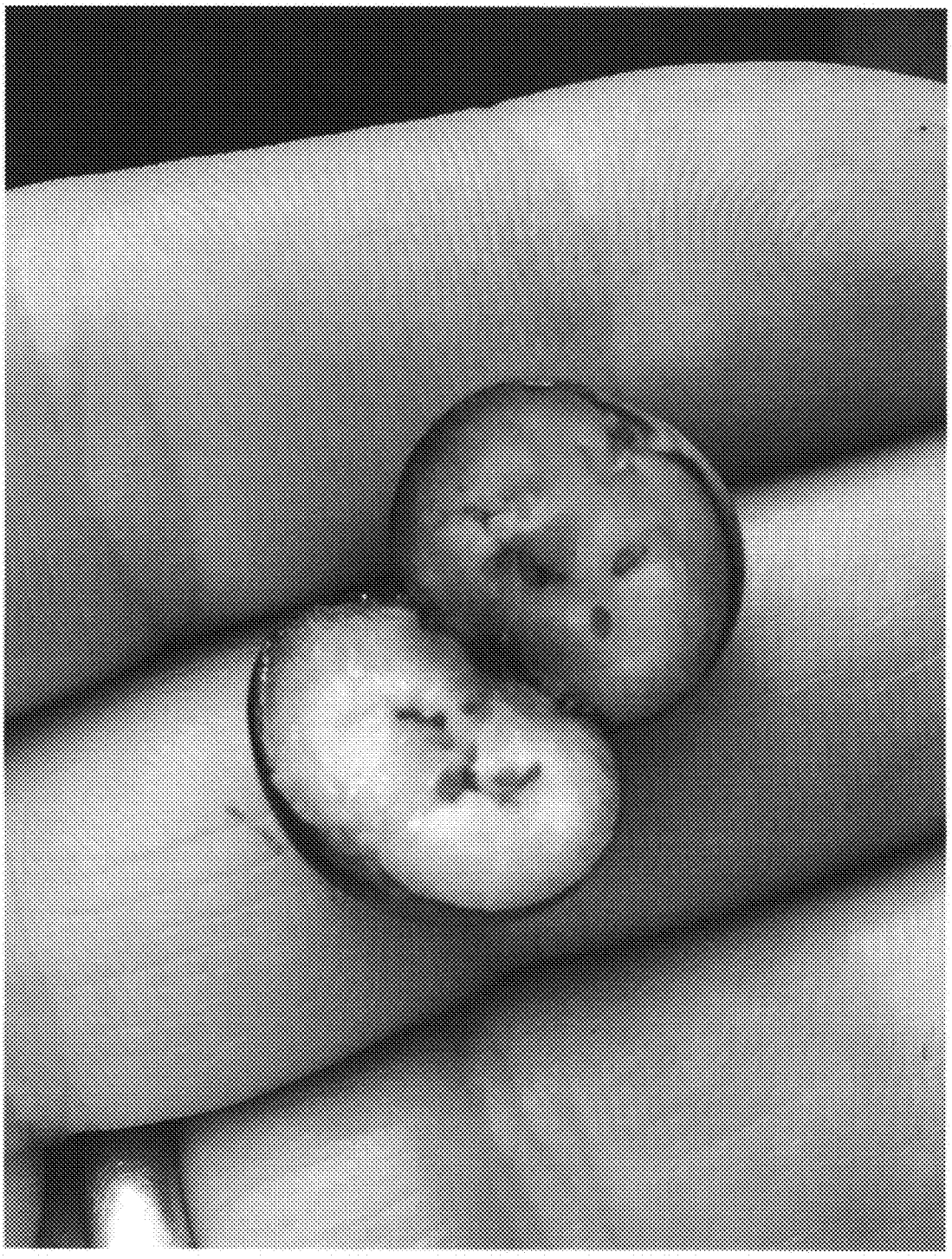

The colors shown are as true as can be reasonably obtained by conventional photographic procedures. The photographs include plants approximately five years' old grown in optimum conditions in Gordonton, Waikato, New Zealand FIG. 1 shows the plant habit
FIG. 2 shows a close-up of a mature leaf upper side
FIG. 3 shows mature leaves upper and under side and one year wood
FIG. 4 shows an open flower and flower buds
FIG. 5 shows unripe and ripe berries
FIG. 6 shows ripe berries
FIG. 7 shows berry flesh and seeds from a ripe berry

DESCRIPTION OF THE NEW CULTIVAR

The following detailed description sets forth the distinctive characteristics of 'JAAC'. The following observations, measurements and values were made on five year old plants, and managed under standard orchard practice. Random measurements of each characteristic were obtained from samples of two plants unless otherwise stated.

Horticultural terminology is used in accordance with UPOV guidelines for *Vaccinium*. All dimensions are in millimetres, and all weights are in grams (unless otherwise stated). Certain characteristics of this variety, such as growth and color, may change with changing environmental conditions (e.g., light, temperature and moisture), nutrient availability, or other factors. Color readings were taken in natural light. Color references are primarily to The 1995 Edition of The Colour Chart published by The Royal Horticultural Society, London (R.H.S.), except where general colours of ordinary significance are used.

DETAILED BOTANICAL DESCRIPTION

Classification:
*Family.*—Ericaceae.
*Botanical name.*—*Vaccinium corymbosum.*
*Common name.*—Blueberry.

Parentage:
*Female parent*.—Unknown.
*Male parent*.—Unknown.
Plant:
*Plant habit*.—Upright plant with erect multiple canes, good vigour.
*Plant height*.—Average 120 cm.
*Plant width*.—Average 100 cm.
*Propagation*.—Softwood cuttings.
Branches:
*Texture of new wood*.—Smooth with inconspicuous lenticels.
*Colour of new wood*.—Yellow-green, RHS 144B with red-purple anthocyanin colouration RHS 60B.
*Texture of one year wood*.—Smooth with inconspicuous lenticels.
*Colour of one year wood*.—RHS 144B with red-purple anthocyanin colouration RHS 60B.
*Texture of three year wood*.—Rough and barky.
*Colour of three year wood*.—Grey-green, RHS 197D.
*Diameter of three year wood*.—10 mm to 20 mm.
Leaves:
*Arrangement*.—Alternate and decussate.
*Length* (*young leaf*).—44 mm to 54 mm.
*Width* (*young leaf*).—30 mm to 35 mm.
*Length* (*mature leaf*).—55 mm to 80 mm.
*Width* (*mature leaf*).—32 mm to 55 mm.
*Shape*.—Broadly ovate.
*Apex*.—Broadly acute.
*Base*.—Attenuate.
*Margin*.—Entire.
*Texture*.—Upper surface: matt, leathery with raised puckering. Lower surface: matt, smooth.
*Colour*.—Young leaves, upper surface: green, RHS 137A. Young leaves, lower surface: green, RHS 138B. Mature leaves, upper surface: green, RHS 137A with red-purple anthocyanin colouration RHS 60B. Mature leaves, lower surface: green, RHS 138B with red-purple anthocyanin colouration RHS 60B.
*Venation*.—Pattern: reticulate. Colour, upper surface: RHS 139C with red-purple anthocyanin colouration RHS 60A on main vein and RHS 60D on lateral veins. Colour, lower surface: RHS 139D with red-purple anthocyanin colouration RHS 60A on main vein and RHS 60D on lateral veins.
*Petiole* (*leaf stem*).—Length: 3 mm to 7 mm. Diameter (cross section) 1 mm to 2 mm. Colour: yellow-green, RHS 144B with red-purple anthocyanin colouration RHS 60B. Texture: smooth.
Inflorescence:
*Fragrance*.—Lightly scented in the early morning.
*Longevity of viable flowers on the plant*.—14 days.
*Peduncle* (*stalk holding each flower cluster*).—Length: 1 mm to 2 mm. Diameter: 2 mm to 4 mm. Colour: yellow-green, RHS 144B with red-purple anthocyanin colouration RHS 60B.
*Pedicel* (*stalk holding each flower*).—Length: 4 mm to 5 mm. Diameter: 2 mm to 4 mm. Colour: yellow-green, RHS 144B with red-purple anthocyanin colouration RHS 60B.
*Flowers*.—Number of bud clusters per fruiting (terminal) shoot: 5-12. Flower number per cluster: 4-7. Colour of flower bud: white, RHS 155B with occasional red-purple anthocyanin colouration RHS 58B on outside near calyx. Shape of flower: urceolate. Colour of corolla (fully opened): white RHS 155B. Length of corolla tube: 9 mm to 11 mm. Width of corolla tube: 7.5 mm to 8 mm. Width of corolla tube aperture: 4 mm to 5 mm.
*Calyx*.—Quantity of lobes: 5. Length of lobes: 4 mm (average). Width of lobes: 3.5 mm (average). Apex of lobes: broadly acute. Margin: smooth. Texture: smooth. Colour: yellow-green, RHS 144B with occasional red-purple anthocyanin colouration RHS 60B on margin.
Reproductive organs:
*Style*.—Quantity: 1. Length: 10 mm to 12 mm. Attitude: erect. Colour: yellow-green, RHS 144B.
*Stamens*.—Quantity: 10.
*Filaments*.—Colour: yellow-green, RHS 144D. Texture: lightly pubescent.
*Anthers*.—Colour: greyed-orange, RHS 167A.
*Ovary*.—Shape: round. Colour: yellow-green, RHS 144D.
*Ovules*.—Colour: yellow-green, RHS 144D with dark brown internal markings.
Fruit:
*Yield*.—High, average 3 kg per 5 year old bush.
*Colour*.—Colour of unripe berry: red-purple RHS 60B. Ripe berry colour with bloom: blue, RHS 103A. No red colouration around stem end of ripe berry. Ripe berry colour without bloom: black, 202A. Abundance of surface bloom: high. Berry flesh colour: green-yellow, RHS 1D.
*Calyx*.—Calyx width: 6 mm to 8 mm. Calyx depth: 2 mm to 3 mm. Calyx shape: five lobed.
*Berry shape*.—Oblate.
*Berry weight range*.—2.5 g to 3 g.
*Average berry weight*.—2.5 g.
*Berry diameter*.—16 mm (average).
*Berry depth*.—11 mm (average).
*Aspect* (*H/W*): 1.45.
*Cluster density*.—Open.
*Detachment force*.—Medium-firm.
*Pedicel* (*fruit stem*) *scar size*.—Average 2.5 mm.
*Pedicel* (*fruit stem*) *scar dryness*.—Dry.
*Berry firmness*.—
*Flavour*.—Taste: sweet flavourful. Texture: smooth, very little grit, crisp to bite. Brix level at consumption: 16% average.
*Suitability for mechanical harvest*.—Not considered.
Seed:
*Seed abundance*.—20 to 25 per berry.
*Seed colour*.—Greyed-orange, RHS 166B.
*Seed size*.—Very small 1 mm average.
Crop timing:
*Vegetative bud burst*.—October to November.
*Beginning of flowering*.—September.
*Beginning of fruit ripening*.—Late January.
*Fruit harvest period*.—1 February to 1 May.
*Leaf senescence*.—Late season deciduous.
Disease resistance: No observations made.
Insect resistance: No observations made.

COMPARISON WITH PARENTAL AND KNOWN CULTIVARS

When compared to the commercial variety 'Sunset Blue' (U.S. Plant Pat. No. 21,761); 'JAAC' has a more upright plant habit, is later fruiting and has later leaf senescence.

When compared to the commercial variety 'O'Neal' (unpatented); 'JAAC' has a broader leaf, a puckered upper leaf texture and a larger average berry size.

When compared to the commercial variety 'Maru' (unpatented); 'JAAC' has more vigorous growth, denser branches, is deciduous, and berries are oblate, larger with thinner skin and smoother texture.

We claim:

1. A new and distinct cultivar of blueberry plant as shown and described herein.

* * * * *